United States Patent [19]
Cope et al.

[11] Patent Number: 5,690,656
[45] Date of Patent: Nov. 25, 1997

[54] METHOD AND APPARATUS FOR CREATING ABDOMINAL VISCERAL ANASTOMOSES

[75] Inventors: Constantin Cope, Elkins Park, Pa.; Hans A. Timmermans, Portland, Oreg.

[73] Assignee: Cook Incorporated, Bloomington, Ind.

[21] Appl. No.: 496,125

[22] Filed: Jun. 27, 1995

[51] Int. Cl.$^6$ .................................................. A61B 17/00
[52] U.S. Cl. .......................... 606/153; 606/151; 128/898
[58] Field of Search ...................................... 606/156, 155, 606/153, 151; 128/898; D13/183; 403/DIG. 1; 335/285, 302–306

[56] References Cited

U.S. PATENT DOCUMENTS

| | | | |
|---|---|---|---|
| 2,697,642 | 12/1954 | Rudy | 403/DIG. 1 |
| 2,953,970 | 9/1960 | Maynard | 335/285 |
| 3,041,697 | 7/1962 | Budreck | 335/285 |
| 3,372,443 | 3/1968 | Daddona, Jr. | 335/302 |
| 3,986,493 | 10/1976 | Hendren, III | 128/1.3 |
| 4,294,255 | 10/1981 | Geroc . | |
| 4,643,604 | 2/1987 | Enrico | 335/306 |
| 5,250,057 | 10/1993 | Chen | 606/153 |
| 5,425,763 | 6/1995 | Stemmann | 403/DIG. 1 |

FOREIGN PATENT DOCUMENTS

| | | | |
|---|---|---|---|
| 7400096 | 7/1975 | Netherlands | 606/153 |
| 736966 | 5/1980 | U.S.S.R. . | |
| 1179978 | 9/1985 | U.S.S.R. . | |
| 1438738 | 11/1988 | U.S.S.R. | 606/153 |
| 1796863 | 10/1992 | U.S.S.R. . | |

*Primary Examiner*—Jeffrey A. Schmidt
*Attorney, Agent, or Firm*—Woodard, Emhardt, Naughton, Moriarty & McNett

[57] ABSTRACT

A method and apparatus for creating abdominal visceral anastomoses. A first magnet is placed within a first viscera and a second, larger magnet is placed within a second viscera. The magnets each have a raised rim around their perimeters. The two magnets couple to each other by virtue of their mutual attraction, thereby capturing a portion of the intervening visceral walls between them. The coupling of the magnets is automatically self-centering, as the smaller magnet is forced to rest within the raised rim of the larger magnet. Additionally, the raised rim of the smaller magnet acts as a fine cutting edge in order to accelerate the process of ischemic necrosis of the tissue captured between the two magnets, thereby forming the anastomosis. Use of the present invention avoids the need for general anesthesia and a laparotic incision, resulting in fewer surgical and post-surgical complications.

23 Claims, 7 Drawing Sheets

METHOD AND APPARATUS FOR CREATING ABDOMINAL VISCERAL ANASTOMOSES

TECHNICAL FIELD OF INVENTION

The present invention relates generally to the creation of an anastomosis between two hollow viscera, and more particularly to the creation of an anastomosis between two hollow viscera using magnets.

BACKGROUND OF THE INVENTION

Bowel anastomosis is a commonly performed procedure which is used to create a channel between two hollow viscera for the purpose of redirecting intestinal contents or bile in patients who have developed obstruction of the bowel or bile duct due to such conditions as tumor, ulcer, inflammatory strictures, or trauma. Referring to FIG. 1, the relative positions of several organs of the abdominal cavity are shown, including the gall bladder 10, the common bile duct 12, the stomach 14, the duodenum 16 and the jejunum 18 of the small intestine. An inflammatory stricture 20 of the jejunum is illustrated, which obstructs passage through the jejunum 18. The complex surgical procedure required in the prior art to correct such a bowel obstruction is illustrated in FIG. 2. Under general anesthesia, a laparotomy is performed in which the bowel segment 22 containing the inflammatory stricture 20 is cut from the jejunum 18. The cut edges of the jejunum 18 are placed together in exact apposition so that sutures 24 may be placed around the circumference in order to form a water tight channel.

Because of the difficulty in forming the sutures 24, also because of the serious complications which can arise if gastric juices leak from the sutures 24, it has been proposed in the prior art to use magnets to couple the two halves of the intestine 18 in order to form a water tight seal and urge the two halves to grow together. Such an arrangement has been proposed in U.S.S.R. Inventors' Certificate No. 1,179,978 to MyShkin et al. and is illustrated in FIG. 3. After resection of the obstructed bowel segment, toroidal magnets 30 and 32 are positioned near the open ends of intestinal segments 34 and 36, respectively. The magnetic attraction between opposite poles of magnets 30 and 32 cause the intestinal segments 34 and 36 to be brought together in uniform alignment, compressing the ends of the intestinal segments 34 and 36 between the magnets 30 and 32. Over the course of a few days, the tissue immediately outside the circumference of the magnets 30 and 32 will grow together, joining the two intestinal portions 34 and 36. The tissue within the circumference of the magnets 30 and 32 is compressed tightly due to the magnetic attraction between the two magnets, thereby reducing the blood supply to this portion of the tissue. After a few days, the process of ischemic necrosis causes this tissue to die and become separated from the healthy tissue on the walls of the intestine. When this occurs, the magnets 30 and 32, as well as the dead tissue held between them, are flushed out through the bowel. The magnets 30 and 32 are provided with large diameter center holes in order to allow passage of the intestinal contents prior to the formation of the necrosis.

The process of ischemic necrosis caused by the compression of two magnets has also been used to cure short strictures of the esophagus in U.S.S.R. Inventor's Certificate No. 736,966. As illustrated in FIG. 4, an esophagus 40 has a short stricture 42 which prevents passage of food through the esophagus 40. A guide wire 44 is introduced into the esophagus 40 and a first magnet 46 is orally introduced into the esophagus 40 over the guide wire 44, until the magnet is near the stricture 42. A second magnet 48 is introduced through a gastrostomy over the guide wire 44 until it rests near the other side of the stricture 42. A first thread 50 is looped through a transverse hole in the magnet 46 prior to introduction into the esophagus 40, while a second thread 52 is looped through a transverse hole in the magnet 48 prior to introduction into the esophagus 40. The ends of the threads 50 and 52 extend outside of the body, and the magnets 46 and 48 may be moved toward the stricture 42 by pulling on the appropriate end of the threads 50 and 52. Once the magnets 46 and 48 are near enough to the stricture 42, their common magnetic attraction pulls them together and locks them in place around the stricture 42. After necrosis has taken place, the magnets 46 and 48 are extracted through the mouth or gastrostomy using the threads 50 and 59.

Magnets have additionally been used in the prior art to facilitate the formation of anastomoses between adjacent viscera. Referring now to FIG. 5, bile produced by the liver (not shown) and stored by the gall bladder 10 is introduced into the jejunum 18 through the common bile duct 12. In cases when the common bile duct 12 becomes obstructed, such as by inflammatory stricture 60, it becomes necessary to make an alternate connection between the common bile duct 12 and the duodenum 16. A method for forming such an anastomosis is disclosed in U.S.S.R. Inventors' Certificate No. 1,769,863 to Kanshin et al.

Referring to FIG. 6, an anastomosis between the common bile duct 12 and the duodenum 16 (choledochoduodenoanastomosis) is formed by inserting surgical tool 62 into the common bile duct 12 until the distal end of the tool 62 is adjacent the stricture 60. The duodenum 16 is then manually compressed and a needle 64 from the tool 62 is used to puncture a wall of the common bile duct 12 and both walls of the duodenum 16. A thread 66 is then inserted through an opening in the needle 64 and the tool 62 and needle 64 are withdrawn from the common bile duct 12, leaving the ends of the guide thread protruding from both the bile duct 12 and the duodenum 16. Referring now to FIG. 7, magnets having through-holes are guided into position over the two ends of the guide thread 66. An incision in one wall of the duodenum 16 is necessary for this procedure. A knot 68 is tied to the end of the thread behind the first magnet 70 prior to insertion of the first magnet 70 into the common bile duct 12. The second magnet 72 is inserted into the duodenum 16 over the guide thread 66 and a plastic retaining ring 74 is then also passed over the guide thread 66. The guide thread 66 is then tied to the plastic retaining ring 74 inside the duodenum 16 such that the magnets 70 and 72 are guaranteed to be properly aligned. The final arrangement is illustrated in FIG. 8. The use of the thread 66 to tie the magnets 70 and 72 together is required in order to guarantee that the magnets 70 and 72 will be properly aligned. Proper alignment is necessary to form a clean anastomosis between the two viscera.

Although the prior art magnetic method illustrated in FIGS. 5–8 represents an improvement over prior surgical techniques for creating the anastomosis, the prior art procedure still requires general anesthesia and a laparotomy in order to place the magnets 70 and 72. Such an invasive and complex surgical procedure can be associated with serious post-operative complications. It is desirable to avoid such surgical procedures whenever possible. Because the most invasive aspect of the prior art surgery is required in order to guarantee proper alignment of the two magnets, there is a need in the prior art for developing a surgical procedure that will guarantee alignment of the magnets without the need for invasive surgery.

SUMMARY OF THE INVENTION

The present invention relates to a method and apparatus for creating abdominal visceral anastomoses. A first magnet is placed within a first viscera and a second, larger magnet is placed with a second viscera. The magnets each have a raised rim around their perimeters. The two magnets couple to each other by virtue of their mutual attraction, thereby capturing a portion of the intervening visceral walls between them. The coupling of the magnets is automatically self-centering, as the smaller magnet is forced to rest within the raised rim of the larger magnet. Additionally, the raised rim of the smaller magnet acts as a fine cutting edge in order to accelerate the process of ischemic necrosis of the tissue captured between the two magnets, thereby forming the anastomosis. Use of the present invention avoids the need for general anesthesia and a laparotic incision, resulting in fewer surgical and post-surgical complications.

In one form of the invention, a device for forming an anastomosis between adjacent viscera is disclosed, comprising a magnet having opposing first and second faces; and a jacket having opposing first and second rim, said jacket formed around a periphery of the magnet on a surface connecting the first and second faces; wherein the first and second jacket rims are spaced farther apart that the first and second magnet faces.

In another form of the invention, a method for forming an anastomosis between first and second adjacent viscera is disclosed, comprising the steps of: (a) inserting a first magnet into a viscera adjacent a digestive tract; (b) inserting a second magnet into a stomach of the digestive tract, wherein the second magnet travels down the digestive tract until it is attracted to the first magnet and coupled thereto through a digestive tract wall and a visceral wall in a self-centering engagement; and (c) allowing tissue compressed between the first and second magnets to undergo ischemic necrosis.

In another form of the invention, a method for forming an anastomosis between first and second adjacent viscera is disclosed, comprising the steps of: (a) inserting a first magnet into a first viscera; (b) inserting a second magnet into a second viscera, wherein the second magnet is attracted to the first magnet and coupled thereto through first and second visceral walls in a self-centering engagement; and (c) allowing tissue compressed between the first and second magnets to undergo ischemic necrosis.

In another form of the invention, a method for forming an anastomosis between first and second portions of a digestive tract is disclosed, comprising the steps of: (a) inserting a first magnet into a stomach; (b) waiting a period of time while the first magnet travels down the digestive tract; (c) inserting a second magnet into the stomach, wherein the second magnet is attracted to the first magnet and coupled thereto through first and second walls of the digestive tract in a self-centering engagement; and (d) showing tissue compressed between the first and second magnets to undergo ischemic necrosis.

DESCRIPTION OF THE PREFERRED EMBODIMENT

Figure 1:
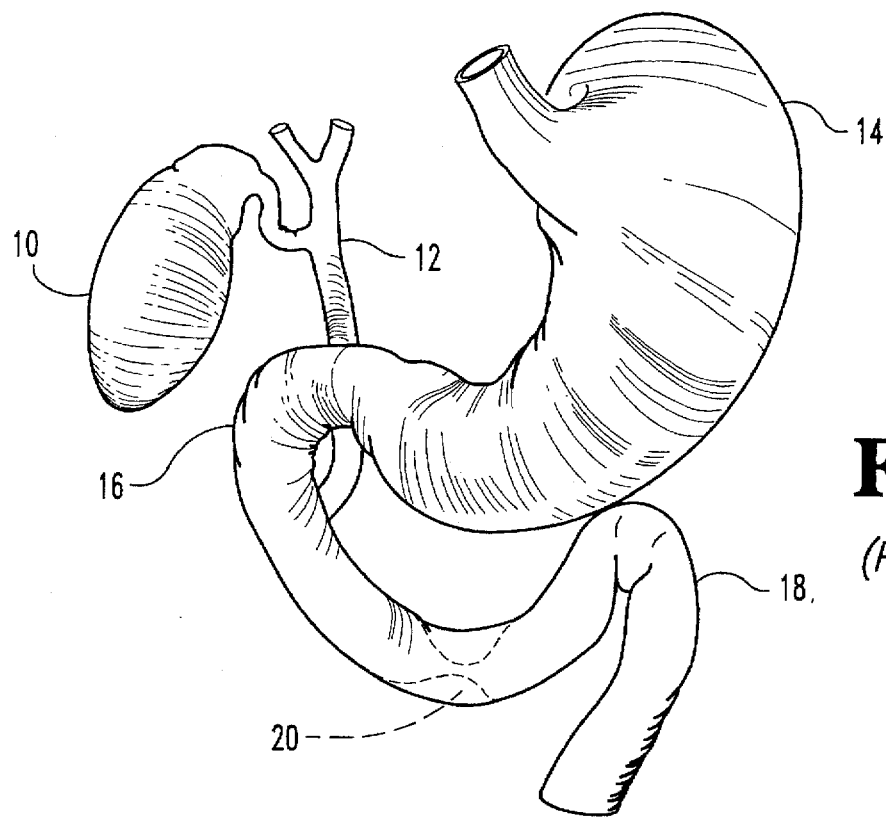
FIG. 1 is an illustration of various abdominal organs, showing an obstruction of the jejunum.
Figure 2:
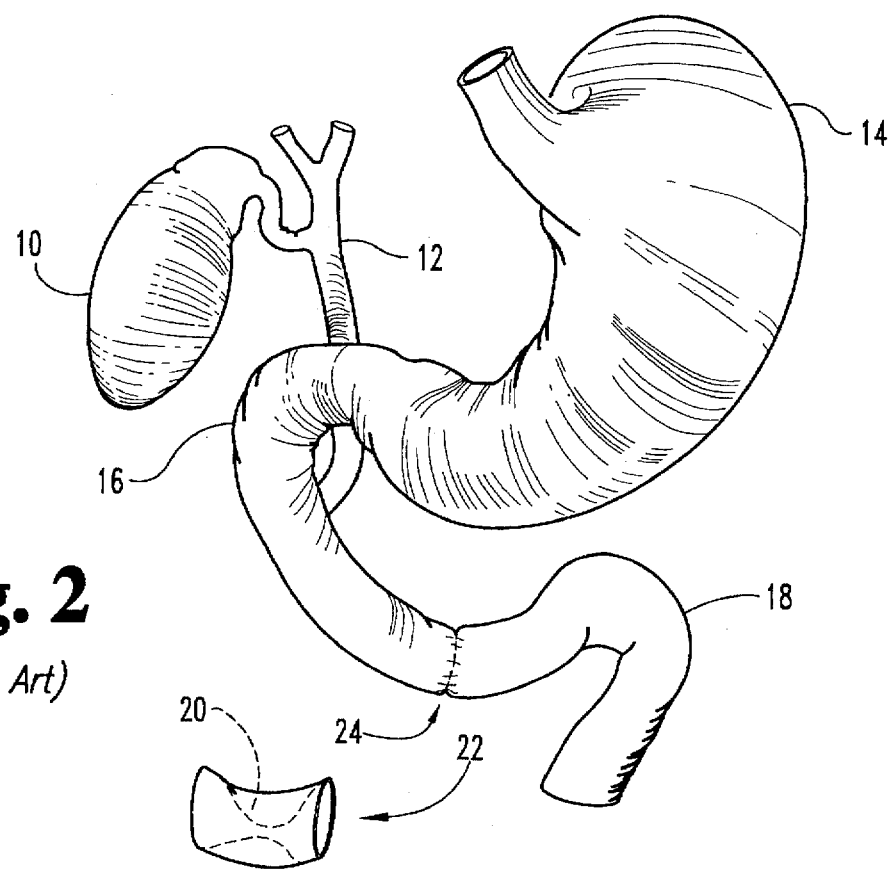
FIG. 2 is an illustration of a prior art surgical procedure for removing an obstruction to the jejunum.
Figure 3:
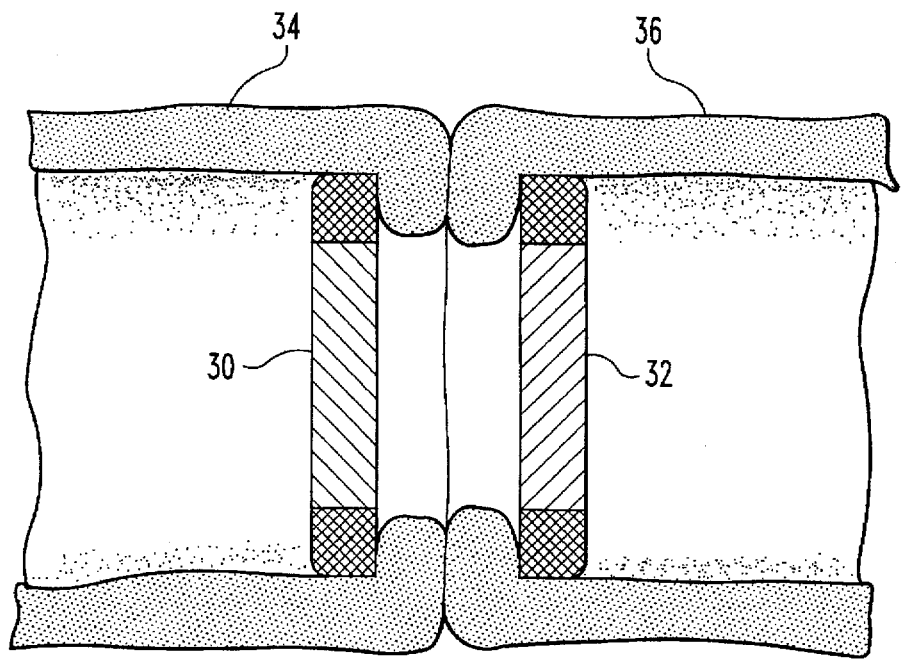
FIG. 3 is a cross-sectional illustration of a prior art device for joining two intestinal segments using magnets.
Figure 4:
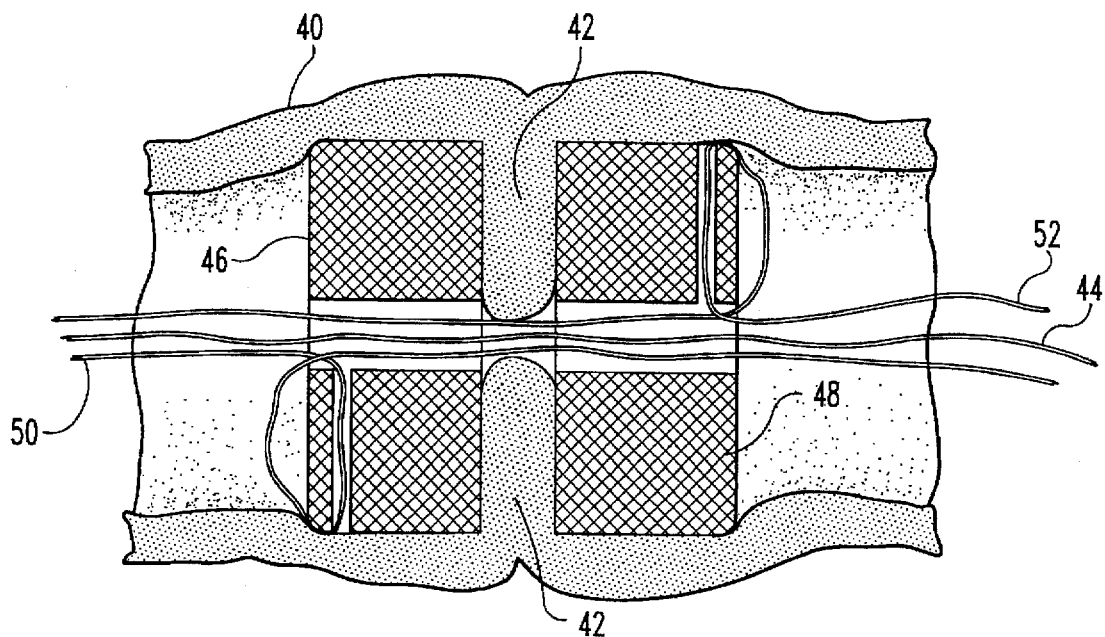
FIG. 4 is a cross-sectional drawing illustrating a prior art method of removing a short stricture of the esophagus using magnets.
Figure 5:
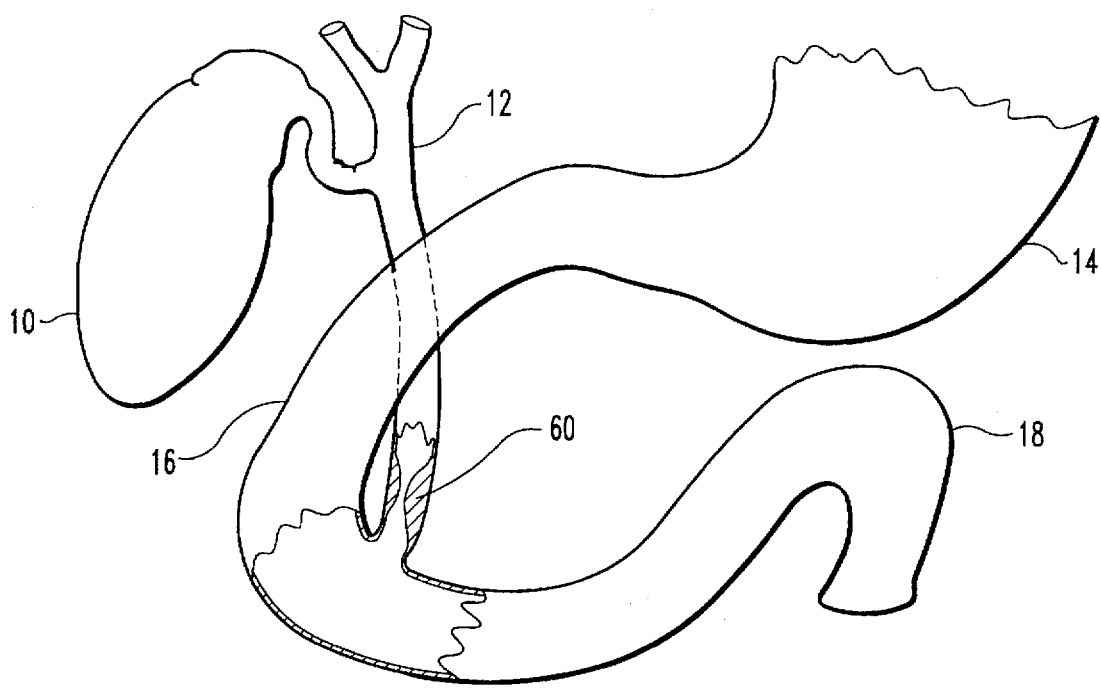
FIG. 5 is a cross-sectional illustration of several abdominal organs, showing a stricture of the common bile duct.
Figure 6:
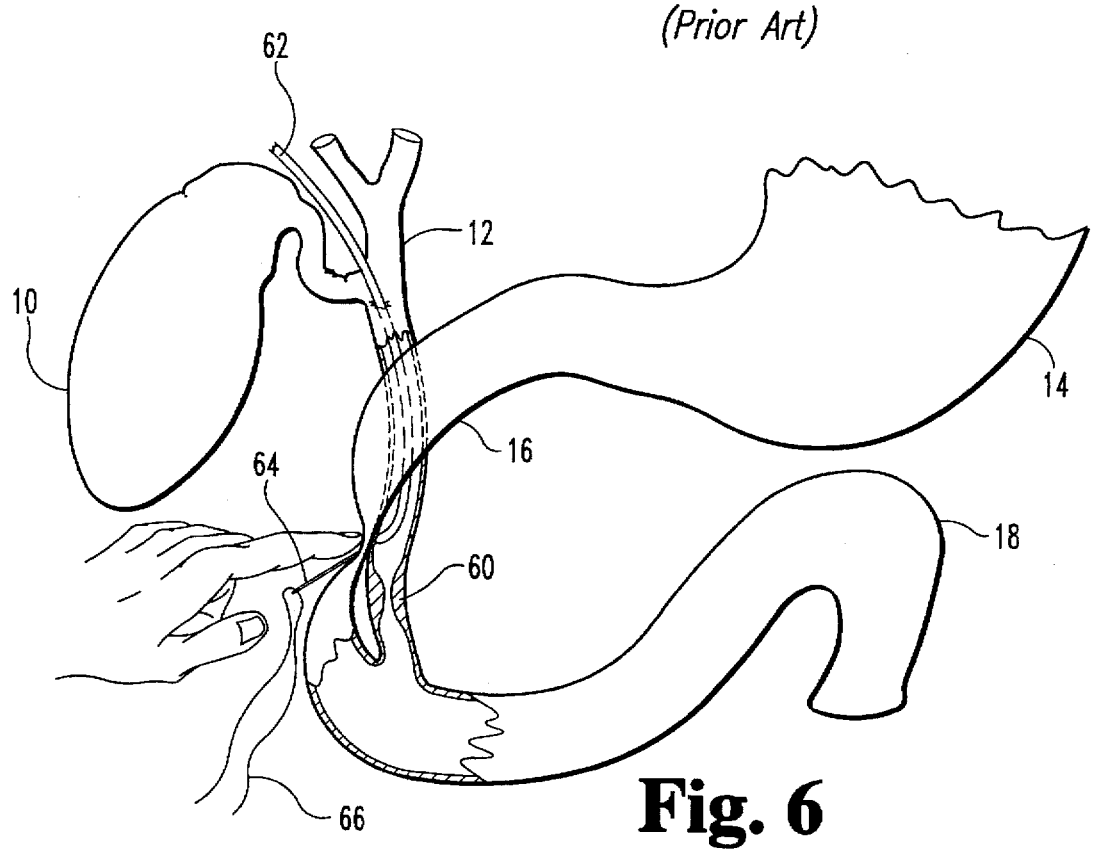
FIGS. 6–7 are partial cross-sectional illustrations of a prior art surgical technique for creating an anastomosis between the common bile duct and the duodenum using magnets.
Figure 7:
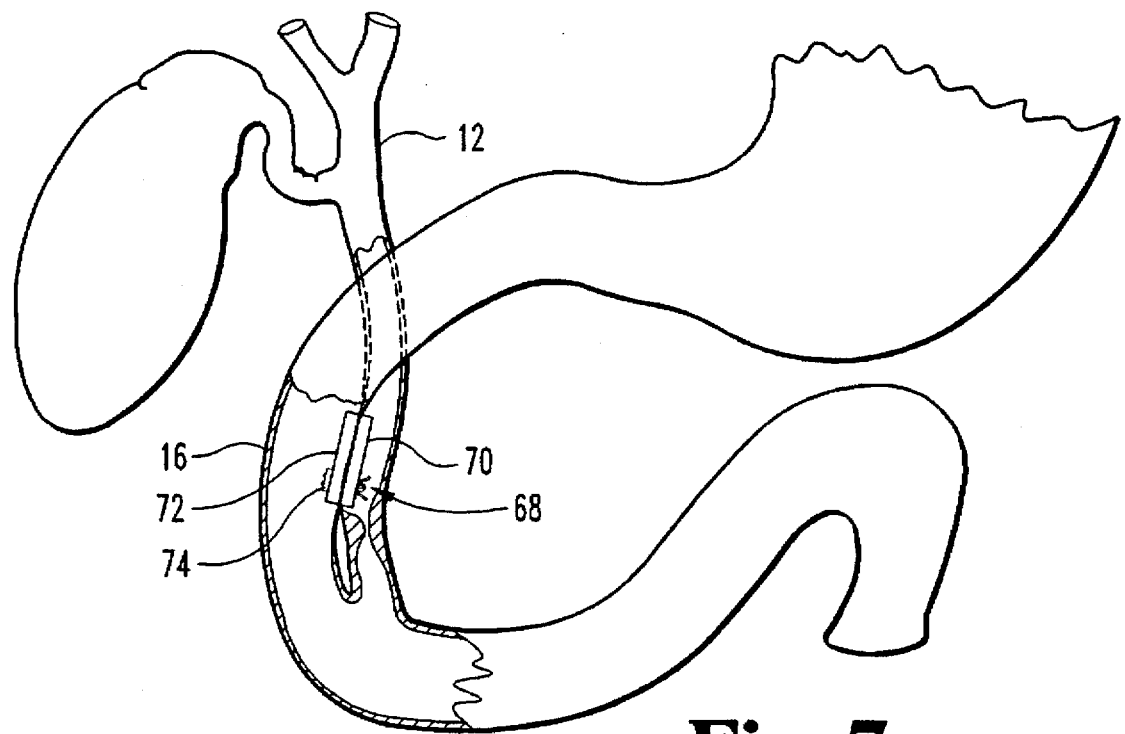
Figure 8:
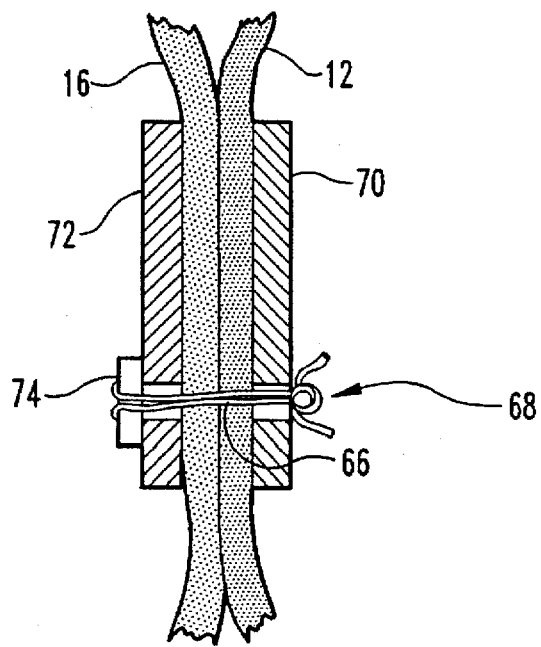
FIG. 8 is a cross-sectional diagram of the two magnets used in the prior art surgical procedure of FIG. 6–7.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Many of the benefits achieved by the magnetic devices of the prior art, such as the creation of an anastomosis without cutting and suturing, are relatively inconsequential due to the fact that general anesthesia and laparotic surgery are still required in order to place and secure the magnets at the proper location. The present invention is therefore directed toward magnet pairs that are self aligning and which therefore require internal invasion into the patient's body for placement.

Figure 9:
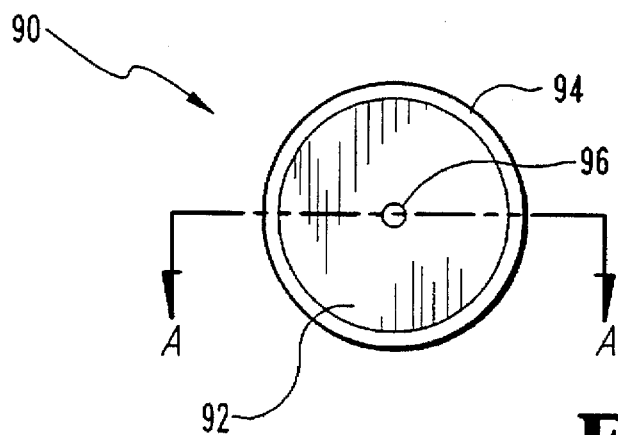
FIG. 9 is a plan view of a first embodiment magnet of the present invention.
Figure 10:
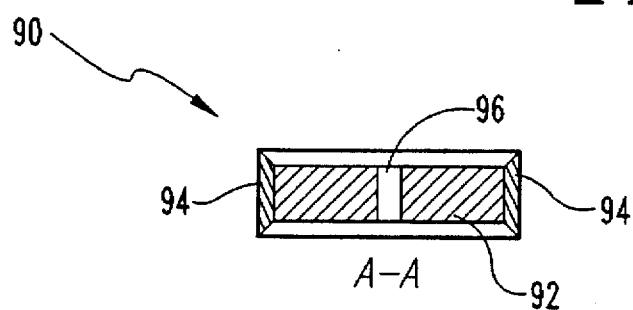
FIG. 10 is a cross-sectional view of the magnet of FIG. 9 taken along section A—A.
Figure 15:
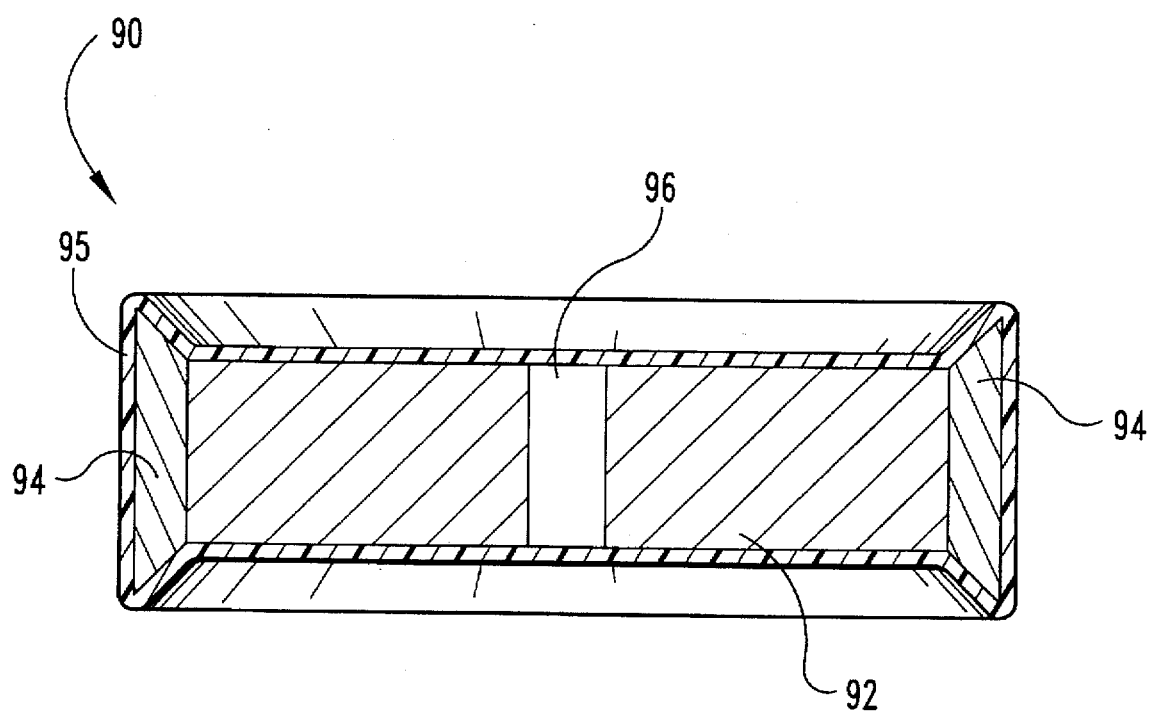
FIG. 15 is a cross-sectional illustration of a fourth embodiment magnet of the present invention.

Referring to FIG. 9, there is illustrated a first embodiment magnet 90 of the present invention. The magnet 90 comprises a magnetic core 92 surrounded by a thin metal rim 94. The magnetic core 92 is preferably a rare-earth magnet, such as Neodymium-iron-boron, cobalt, etc. The magnetic core 92 is magnetized on its largest surface, having a north pole on one side of the magnet and a south pole on the other side of the magnet. The metal jacket 94 is preferably formed from a nonferrous metal which is press fit or adhesively coupled to the magnetic core 92. The metal jacket 94 is formed so as to protrude approximately 1 mm above each side of the magnet 92. The complete magnet assembly 90 is coated with a protective coating 95 (see FIG. 15) such as TEFLON, PARALENE, etc. for protection of the magnetic core 92 and the jacket 94 from the corrosive effects of digestive acids. The magnetic core 92 is pierced by a central hole 96 in order to allow the magnet assembly 90 to be used in conjunction with a guide wire. The magnet 90 is shown in cross-section in FIG. 10. The view of FIG. 10 clearly shows the rim of the metal jacket 94 protruding above each surface of the magnet 92.

Figure 11:
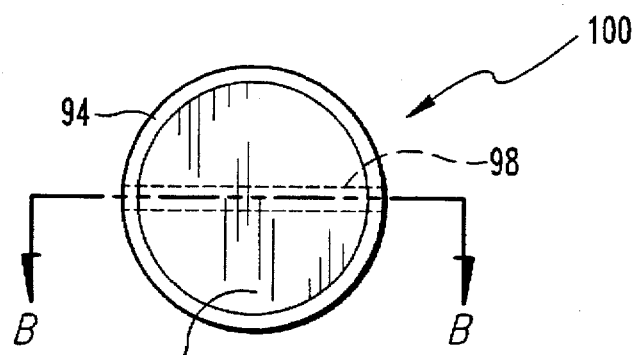
FIG. 11 is a plan view of a second embodiment magnet of the present invention.
Figure 12:
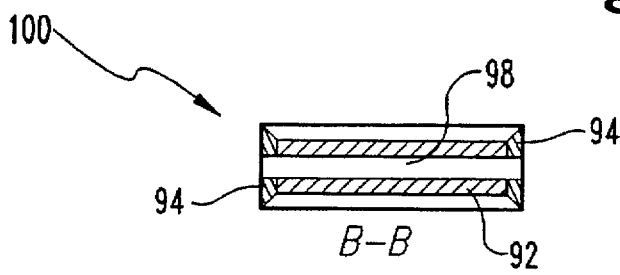
FIG. 12 is a cross-sectional view of the magnet of FIG. 11 taken along the section B—B.

A second embodiment of the magnet assembly 90 is illustrated in FIG. 11 and indicated generally at 100. The magnet assembly 100 includes a magnetic core 92 and metal jacket 94 identical to that of the magnet assembly 90, however instead of an axial hole 96, the magnet assembly 100 includes a transverse hole 98. The transverse hole 98 allows the magnet assembly 100 to be oriented on the guide wire in a position rotated 90° from the position maintained by the magnet assembly 90. The magnet assembly 100 is illustrated in cross-section in FIG. 12. The magnets 90 and 100 are to be manufactured in various sizes and used in pairs of differently sized magnets. For instance, a preferred embodiment of the present invention, the magnets 90 and 100 are manufactured in three sizes. A small magnet is 0.250" in diameter, a medium magnet is 0.375" in diameter and a large magnet is 0.500" in diameter. The holes 96 and 98 are 0.040" in diameter in the preferred embodiment.

Figure 13:
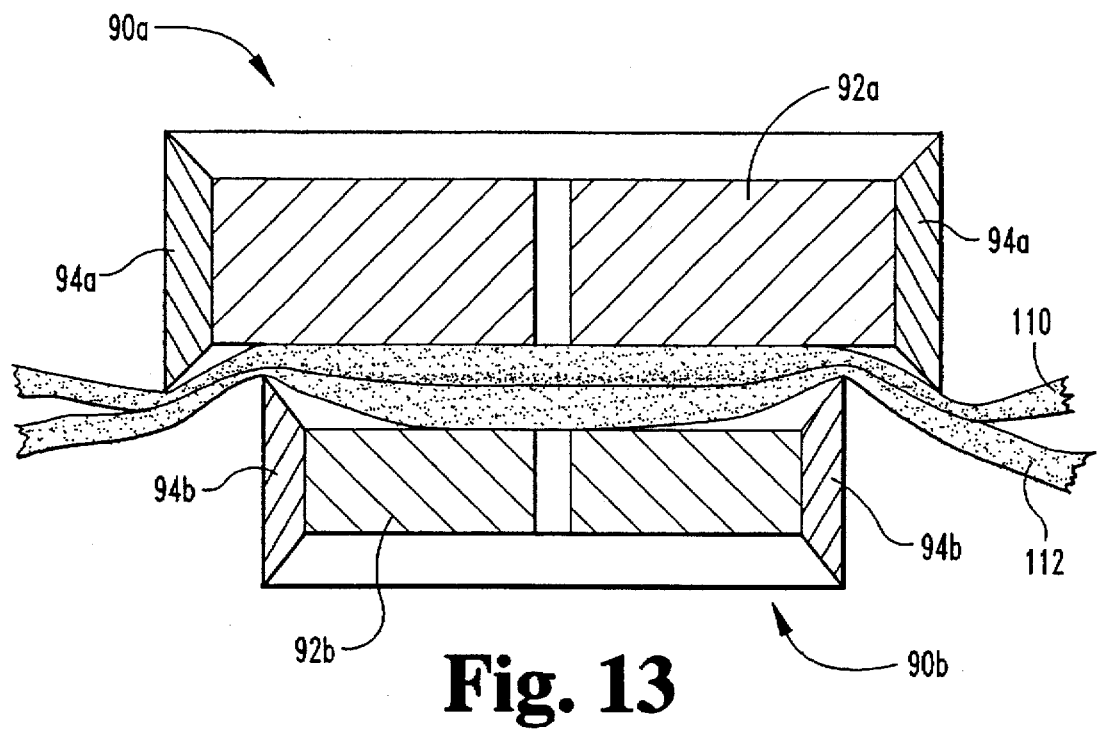
FIG. 13 is a cross-sectional illustration of two magnets of the present invention engaged between two viscera in order to form an anastomosis.

Referring now to FIG. 13, the use of a magnet pair to form an anastomosis is illustrated. In order to form an anastomosis between the walls 110 and 112 of two adjacent viscera, a magnet 90a is placed adjacent the wall 110 and a magnet 90b is placed adjacent the wall 112. The magnetic attraction between the magnets 90a and 90b cause them to move toward one another, thereby capturing a portion of the walls 110 and 112 between them. In a preferred embodiment, it is preferable that the magnet pair 90a and 90b have a minimum separation weight of 500 grams, in order to insure adequate compression of the walls 110 and 112 in the anastomosis area. It will be appreciated that the magnets 90a and 90b are drawn toward one another through the mutual attraction of their magnetic fields, while the metal jacket 94a which forms a ridge raising above the surface of the magnetic core 92a, acts as a barrier to center the magnet 90b within the circumferential confines of the raised rim of the jacket 94a. Because of the automatic centering and alignment provided by the raised rim of the jacket 94a, the magnet assemblies 90a and 90b are self-aligning and no surgical placement and coupling of the magnets in the desired location is required, as with the prior art. Furthermore, the raised rim of the jacket 94b of the smaller magnet assembly 90b acts as a fine cutting edge which accelerates the compression and resulting ischemic necrosis of the walls 110 and 112 between the two magnets. This is due to the fact that all of the force of the magnetic attraction between magnets 90a and 90b is placed upon the very small surface area around the rim of the metal jacket 94b, instead of being spread across a much larger surface area as in the prior art magnets. Such a concentration of the compression forces of the magnet reduce the amount of time necessary to produce an anastomosis between the two viscera.

By providing magnets of various sizes, it is thereby possible to form anastomoses of varying sizes depending upon the size of the magnets chosen. Small magnets may be used to create small anastomoses in small viscera, while larger magnets may be used to create larger anastomoses, such as between the stomach and the jejunum. If a guide wire will not be used to place the magnet, then the center hole 96 or 96 may be omitted, thereby increasing the size and strength of the magnet. Furthermore, the axial center hole 96 may be made larger so that a drainage catheter may be placed through the walls 110 and 112 extending between the magnets' center holes. In this way, a passage is formed between the walls of the two viscera before the anastomosis forms. In a preferred embodiment, the center hole which allows incorporation of a drainage catheter may be sized from 0.110-0.150".

The magnets of the present invention can be used to form an anastomosis between adjacent viscera in only a few days. After that time, the walls interposed between the magnets will become glued together and squeezed into a very thin membrane which eventually loosens from its attachment to the remaining walls by the process of ischemic necrosis. The magnets are then evacuated down the bowel, leaving a functional anastomosis with clean edges and no peritoneal leakage. Several types of anastomoses can be performed with the magnets of the present invention by percutaneous insertion or by simple timed ingestion of the magnets, thereby eliminating the need for invasive laparotomy.

For example, gastro-jejunal anastomosis can be performed by guiding a flexible stainless steel guide wire under fluoroscopy with a selective catheter through the mouth and stomach and into the proem al small bowel which courses close to or behind the stomach. The smaller magnet is then inserted over the guide wire and pushed through the mouth to follow the guide wire to the small bowel. Once the small magnet is in place, the larger magnet is then swallowed or advanced to the stomach by means of the same guide wire. With external massage, the two magnets will then come together by virtue of their magnetic attraction. Once the two magnets are magnetically coupled, the rim of the metal jacket of the larger magnet will ensure that the smaller magnet is centered relative to the larger magnet. In this way, the gastro-jejunal anastomosis is formed without any incision whatsoever.

Alternatively, the first magnet can be swallowed by the patient and its course through the digestive tract followed by means of x-ray or other non-invasive monitoring technique. Once the first magnet is in the location of the desired anastomosis, the second magnet can be swallowed. The magnetic attraction between the two magnets will cause them to couple through the stomach and intestinal walls in a self-centering alignment, eventually producing the anastomosis by ischemic necrosis.

A cholecysto-duodenal or jejunal anastomosis may be performed with the magnets of the present invention whenever the gall bladder and the bowel needs to be connected. A cholecystostomy is first performed in order to insert the smaller magnet within the gall bladder. This can be performed percutaneously with local anesthesia by standard needle-guide wire-dilator techniques as is known in the art. Once the smaller magnet has been placed in the gall bladder, the larger magnet is inserted into the stomach by swallowing or by guide wire technique. Over the next 24 hours, the large magnet will be propelled down the small bowel until it comes close enough to become attracted to the magnet within the gall bladder. At this time, the two magnets will become locked together, the smaller magnet within the gall bladder automatically centering itself with the larger magnet in the stomach by virtue of the rim of the metal jacket surrounding the larger magnet.

A choledoco-jejunal anastomosis may also be performed with the magnets of the present invention whenever the common bile duct becomes obstructed. The smaller magnet is placed within the common bile duct percutaneously with local anesthesia by transhepatically puncturing a dilated intrahepatic bile duct under fluoroscopy, and dilating the tract sufficiently to allow insertion of the small magnet. The larger magnet is then introduced into the stomach by swallowing or by guide wire technique and is allowed to move down the bowel until it connects with the bile duct magnet through the gastric-duodenal or jejunal bowel wall, depending upon the particular anatomy. Once again, the small magnet in the common bile duct will be automatically centered with the large magnet in the bowel because of the raised rim of the metal jacket surrounding the large magnet.

In each of the above examples, the anastomosis is formed without the need for general anesthesia or a laparotic incision, thereby greatly reducing the risk of complication from the procedure. Furthermore, because of the raised cutting surface of the smaller magnet acting against the flat surface of the larger magnet, the anastomosis is formed in a shorter period of time and a cleaner, more accurate cut between the visceral walls is obtained.

Figure 14:
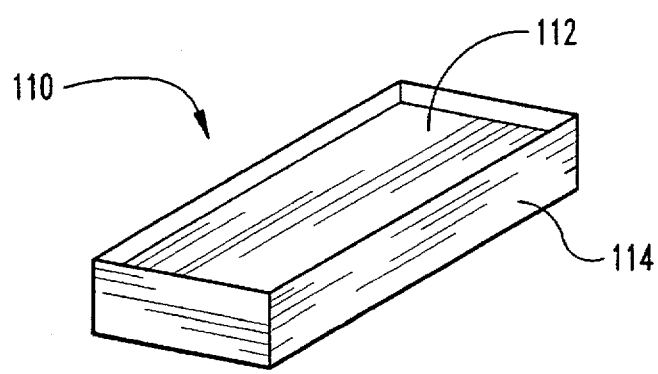
FIG. 14 is a perspective view of a third embodiment magnet of the present invention.

It will be appreciated by those skilled in the art that the self-centering magnets of the present invention may be constructed in any shape suitable for a particular anastomotic procedure. For example, a third embodiment of the present invention is illustrated in FIG. 14 and indicated generally at 110. The magnet assembly 110 is formed in a rectangular configuration and includes a magnetic core 112 surrounded by a metal jacket 114. The rim of the metal jacket 114 extends beyond the planar surface of the magnetic core 112 and provides the same self-centering and accelerated necrosis as the first and second embodiments of the present invention.

It will further be appreciated by those skilled in the art that the self-centering magnets of the present invention may be constructed in any size suitable for a particular anastomotic procedure. For example, much smaller magnets may be used for creating anastomoses between adjacent blood vessels. The size of such magnets is limited only by the prevailing state of magnetic technology, as sufficient magnetic attraction must be exhibited by the magnet pair in order to form the necrosis.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for forming an anastomoses between first and second adjacent viscera, comprising the steps of:
    (a) inserting a first magnet into a viscera adjacent a digestive tract;
    (b) inserting a second magnet into a stomach of the digestive tract, wherein at least one of the first and second magnets includes means for self-centering engagement during magnetic attraction, so that the second magnet travels down the digestive tract until it is attracted to the first magnet and is coupled thereto through a digestive tract wall and a visceral wall in a self-centering engagement; and
    (c) allowing tissue compressed between the first and second magnets by magnetic attraction between the first and second magnets to undergo ischemic necrosis.

2. The method of claim 1, further comprising the step of:
    (d) flushing the first and second magnets out of the digestive tract.

3. The method of claim 1, wherein step (a) is performed percutaneously.

4. The method of claim 1, wherein step (b) is performed by having a patient swallow the second magnet.

5. The method of claim 1, wherein the self-centering engagement is produced by a peripheral raised rim on the second magnet, the rim forcing the first magnet into centered alignment with the second magnet when the first and second magnet engage.

6. The method of claim 1, wherein step (a) further comprises inserting the first magnet into a gallbladder.

7. The method of claim 1, wherein step (a) further comprises inserting the first magnet into a common bile duct.

8. A method for forming an anastomoses between first and second adjacent viscera, comprising the steps of:
    (a) inserting a first magnet into a first viscera;
    (b) inserting a second magnet into a second viscera, wherein at least one of the first and second magnets includes means for self-centering engagement during magnetic attraction, so that the second magnet is attracted to the first magnet and is coupled thereto through first and second visceral walls in a self-centering engagement; and
    (c) allowing tissue compressed between the first and second magnets by magnetic attraction between the first and second magnets to undergo ischemic necrosis.

9. The method of claim 8, further comprising the step of:
    (d) removing the first and second magnets after the anastomosis has formed.

10. The method of claim 8, wherein step (a) is performed percutaneously.

11. The method of claim 8, wherein steps (a) and (b) are performed percutaneously.

12. The method of claim 8, wherein the self-centering engagement is produced by a peripheral raised rim on the second magnet, the rim forcing the first magnet into centered alignment with the second magnet when the first and second magnet engage.

13. The method of claim 8, wherein step (a) further comprises inserting the first magnet into a jejunum and step (b) further comprises inserting the second magnet into a stomach.

14. The method of claim 8, wherein step (a) further comprises inserting the first magnet into a common bile duct and step (b) further comprises inserting the second magnet into a duodenum.

15. A method for form jug an anastomoses between first and second portions of a digestive tract, comprising the steps of:
    (a) inserting a first magnet into a stomach;
    (b) waiting a period of time while the first magnet travels down the digestive tract;
    (c) inserting a second magnet into the stomach, wherein at least one of the first and second magnets includes means for self-centering engagement during magnetic attraction, so that the second magnet is attracted to the first magnet and is coupled thereto through first and second walls of the digestive tract in a self-centering engagement; and
    (d) allowing tissue compressed between the first and second magnets by magnetic attraction between the first and second magnets to undergo ischemic necrosis.

16. The method of claim 15, further comprising the step of:
    (e) flushing the first and second magnets out of the digestive tract.

17. The method of claim 15, wherein step (a) is performed with a guide wire.

18. A device for forming an anastomoses between adjacent viscera, comprising:
    a first magnet having opposing first and second faces;
    a first jacket having opposing first and second rims, said first jacket formed around a first periphery of the first magnet on a first surface connecting the first and second faces, wherein the first and second jacket rims are spaced farther apart than the first and second magnet faces wherein said first and second rims include means for promoting tissue necrosis;

a second magnet having opposing third and fourth faces; and a second jacket having opposing third and fourth rims, said second jacket formed around a second periphery of the second magnet on a second surface connecting the third and fourth faces, wherein the third and fourth jacket rims are spaced farther apart than the third and fourth magnet faces;

wherein the second periphery is smaller than the first periphery, such that the first and second magnets are self-centering when they are magnetically coupled through walls of the adjacent viscera.

19. The device of claim 18, wherein the first and second magnets are rare-earth magnets.

20. The device of claim 18, wherein:

the first rim extends beyond the first face;

the second rim extends beyond the second face;

the third rim extends beyond the third face; and the fourth rim extends beyond the fourth face.

21. The device of claim 18, wherein the first and second jackets are formed from a nonferrous metal.

22. The device of claim 18, further comprising:

a first coating surrounding the first magnet and first jacket assembly; and a second coating surrounding the second magnet and second jacket assembly;

wherein the first and second coatings are acid resistant.

23. The device of claim 18, wherein:

the first magnet includes a first axial hole formed between the first and second faces; and the second magnet includes a second axial hole formed between the third and fourth faces.

* * * * *

UNITED STATES PATENT AND TRADEMARK OFFICE
CERTIFICATE OF CORRECTION

PATENT NO. : 5,690,656
DATED : November 25, 1997
INVENTOR(S) : Constantin Cope et al.

It is certified that error appears in the above-identified patent and that said Letters Patent is hereby corrected as shown below:

In column 1, line 31, please insert --and-- before "also".
In column 2, line 15, please change "59" to --52--.
In column 2, line 42, please change "to" to --in--.
In column 3, line 21, please change "rim" to --rims--.
In column 3, line 54, please change "showing" to --allowing--.
In column 6, line 14, please change "proem al" to --proximal--.
In column 8, line 38, please change "form jug" to --forming--.

Signed and Sealed this

First Day of February, 2000

Attest:

Q. TODD DICKINSON

*Attesting Officer*  *Acting Commissioner of Patents and Trademarks*